(12) United States Patent
Heide et al.

(10) Patent No.: US 10,125,772 B2
(45) Date of Patent: Nov. 13, 2018

(54) METHOD OF MONITORING AN IMPELLER PUMP USED IN A MEDICAL APPLICATION

(71) Applicant: Fresenius Medical Care Deutschland GmbH, Bad Homburg (DE)

(72) Inventors: Alexander Heide, Eppstein (DE); Christoph Wiktor, Gelnhausen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 118 days.

(21) Appl. No.: 15/021,475

(22) PCT Filed: Oct. 13, 2014

(86) PCT No.: PCT/EP2014/002758
§ 371 (c)(1),
(2) Date: Mar. 11, 2016

(87) PCT Pub. No.: WO2015/058841
PCT Pub. Date: Apr. 30, 2015

(65) Prior Publication Data
US 2016/0222969 A1 Aug. 4, 2016

(30) Foreign Application Priority Data
Oct. 24, 2013 (DE) .................. 10 2013 017 828

(51) Int. Cl.
*F04D 15/00* (2006.01)
*A61M 1/10* (2006.01)
*F04D 3/00* (2006.01)

(52) U.S. Cl.
CPC ....... *F04D 15/0088* (2013.01); *A61M 1/1029* (2014.02); *F04D 3/00* (2013.01);
(Continued)

(58) Field of Classification Search
CPC .... F04D 3/00; F04D 15/0077; F04D 15/0088; A61M 1/1006; A61M 1/101;
(Continued)

(56) References Cited

U.S. PATENT DOCUMENTS

2003/0152462 A1* 8/2003 Yaegashi ............... F04D 29/048
417/42
2008/0133008 A1 6/2008 Crosby et al.
(Continued)

FOREIGN PATENT DOCUMENTS

AU 2007229361 11/2012
CN 1084092 3/1994
(Continued)

*Primary Examiner* — Benjamin Schmitt
(74) *Attorney, Agent, or Firm* — Jacobson Holman, PLLC.

(57) ABSTRACT

The invention relates to a method of monitoring an impeller pump used in a medical application, wherein the structure-borne noise arising in the impeller pump is measured and this measured structure-borne noise is compared with a reference curve and/or with a limit value, wherein a signal is output as a sign for a disturbance of the operation of the impeller pump. The invention further relates to a blood treatment apparatus in which the aforesaid method is carried out.

19 Claims, 4 Drawing Sheets

(52) U.S. Cl.
CPC ..... *F04D 15/0072* (2013.01); *F04D 15/0077* (2013.01); *A61M 1/101* (2013.01); *A61M 1/1006* (2014.02); *A61M 1/1012* (2014.02); *A61M 1/1086* (2013.01); *A61M 2205/12* (2013.01); *A61M 2205/3375* (2013.01); *A61M 2205/702* (2013.01)

(58) Field of Classification Search
CPC .............. A61M 1/1012; A61M 1/1029; A61M 1/1086; A61M 2205/12; A61M 2205/3375; A61M 2205/70; A61M 2205/702
USPC .......................................................... 73/168
See application file for complete search history.

(56) References Cited

U.S. PATENT DOCUMENTS

2009/0101550 A1* 4/2009 Muller .................... A61M 1/16
 210/87
2009/0281484 A1* 11/2009 Childers ................. A61M 1/28
 604/29
2010/0269574 A1 10/2010 Zeqiri
2011/0118998 A1 5/2011 Loose et al.

FOREIGN PATENT DOCUMENTS

| | | |
|---|---|---|
| CN | 1401986 | 3/2003 |
| CN | 101829371 | 9/2010 |
| CN | 102076367 | 5/2011 |
| CN | 103249952 | 8/2013 |
| DE | 102009007806 | 8/2010 |
| DE | 102009022107 | 11/2010 |
| DE | 102010027999 | 10/2011 |
| EP | 1972793 | 9/2008 |
| GB | 2451438 | 2/2009 |
| JP | 2004522529 | 7/2004 |
| JP | 2010534791 | 11/2010 |
| JP | 2013515523 | 5/2013 |

* cited by examiner

METHOD OF MONITORING AN IMPELLER PUMP USED IN A MEDICAL APPLICATION

The invention relates to a method and to an apparatus for monitoring an impeller pump used in a medical application and in particular to the detection of functional disturbances of such an impeller pump. In this respect the impeller pump can in particular be arranged in an extracorporeal blood circuit and/or in a dialysate circuit.

It is already known that impeller pumps can be components of a disposable or of a blood hose kit, in particular also of a blood cassette. The impeller of such impeller pumps is as a rule magnetically supported so that the impeller only comes into contact involving friction with the conveyed blood in disturbance-free operation. Such an operation is also called "contactless". However, deviations from disturbance-free operation may also occur. A magnetic is supported in a centered manner in the impeller, for example molded around by means of plastic in an injection molding process. The position of the magnet in the magnetic field of the drive at the machine side is very accurate and can be monitored during operation. However, this does not always have to apply to the injection molded jacket of the magnet in the impeller in dependence on production tolerances.

A first possible disturbance of operation of an impeller pump therefore comprises the fact that the rotating impeller carries out uncontrolled movements, for example due to imbalance, which in the most unfavorable case can result in collisions of the impeller with the housing wall of the impeller pump. There is in this respect a danger of mechanical damage of the blood conveyed between the impeller of the impeller pump and the housing wall of the impeller pump, of so-called hemolysis. However, collisions of the impeller with the housing wall are also wanted on operation of such impeller pumps in the dialysate circuit since they can result in wear and thus in contamination of the dialysate.

Another disturbance can comprise the excessive collection of air bubbles in the impeller pump. Since media of higher density are also displaced radially outwardly due to the rotation of the impeller, the light air bubbles are displaced radially inwardly and collect there. The impeller pump thus acts as a temporary bubble trap. From a certain air bubble size onwards, the air bubbles can no longer easily leave the impeller pump. It is only observed at very high speeds that small air bubbles are carried out with the blood flow as long as only a little air has collected. In continuous operation of the impeller pump, the collected air is carried out with the blood flow on an exceeding of the intake capacity. To prevent this, the air must be led directly out of the impeller pump in specific time intervals. It would be desirable for this purpose to know the amount of the collected air.

It is therefore the object of the present invention to provide a method and an apparatus for monitoring the operation of impeller pumps for disturbances.

This object is achieved in accordance with the invention by the independent claims 1, 8, 13, 15 and 16. The dependent claims contain preferred embodiments of the invention.

In this respect, the invention comprises a method of monitoring an impeller pump used in a medical application by means of structure-borne noise analysis comprising the following steps:
- measuring the structure-borne noise arising in the impeller pump;
- comparing the measured structure-borne noise of the impeller pump with a first reference curve and/or with a first limit value;
- concluding a disturbance of the operation of the impeller pump when the measured structure-borne noise of the impeller pump differs from the reference curve and/or exceeds the limit value;
- outputting a signal as a characteristic for a disturbance of the operation of the impeller pump.

The fact is exploited in the solution in accordance with the invention that the impeller in the impeller pump generates structure-borne signals, which are evaluated, in operation by occasional collision with the pump head or by carried in air bubbles.

Special embodiments of the invention result from the subordinate claims dependent on the main claim.

In a possible embodiment of the present invention, the air amount in the impeller pump can be detected using the aforesaid method.

In this respect, a venting of the impeller pump can be carried out when the detected air amount and/or the measured structure-borne noise of the impeller pump differ from the reference curve and/or exceed the limit value.

In a possible embodiment, for this purpose, the collected air is led off via a venting opening of the impeller pump chamber.

The collisions of the impeller of the impeller pump with the housing of the impeller pump can be detected as a further disturbance.

In accordance with the invention, the measurement of the structure-borne noise can take place during the operation of the impeller pump. A monitoring of the impeller pump during the ongoing operation of the medical application is thus in particular possible.

In this respect, the impeller pump can be arranged in a medical apparatus, in particular in a dialysis machine, and particularly preferably in a dialysis machine for carrying out a hemodialysis or a hemofiltration or a hemodiafiltration or a peritoneal dialysis.

The impeller pump can furthermore be arranged in an extracorporeal blood circuit or in a dialysate circuit of the dialysis machine.

In particular, the method in accordance with the invention can be used in this respect for monitoring a first impeller pump arranged in an extracorporeal blood circuit for carrying out hemodialysis, hemofiltration or hemodiafiltration and/or for monitoring a second impeller pump arranged in a dialysate circuit for carrying out hemodialysis or hemodiafiltration or peritoneal dialysis based on the analysis of structure-borne noise and comprises the following steps:
- operating the extracorporeal blood circuit by means of controlling the first impeller pump and/or operating the dialysate circuit by means of controlling the second impeller pump;
- measuring the structure-borne noise arising in the first impeller pump and/or measuring the structure-borne noise arising in the second impeller pump;
- comparing the measured structure-borne noise of the first impeller pump with a first reference curve and/or with a first limit value; and/or comparing the measured structure-borne noise of the second impeller pump with a second reference curve and/or with a second limit value;
- concluding a disturbance of the operation of the first impeller pump when the measured structure-borne noise of the first impeller pump differs from the first reference curve and/or exceeds the first limit value; and/or concluding a disturbance of the operation of the second impeller pump when the measured structure-borne noise of the second impeller pump differs from the second reference curve and/or exceeds the second limit value;

outputting a signal as a sign for a disturbance of the operation of the first impeller pump and/or outputting a signal as a sign for a disturbance of the operation of the second impeller pump.

In accordance with the invention, the air quantity in the impeller pump can be detected using the aforesaid method.

The collisions of the impeller of the impeller pump with the housing of the impeller pump can be detected as a further disturbance.

In accordance with the invention, a first structure-borne noise sensor is provided at the first impeller pump and a second structure-borne noise sensor is provided at the second impeller pump for converting the structure-borne noise info electrical signals. The drive unit of the respective impeller pump can, for example, have the structure-borne noise sensor. The first structure-borne noise sensor and/or the second structure-borne noise sensor each has/have signal lines for transferring the electrical signals to a control and processing unit.

The present invention furthermore comprises a medical apparatus which carries out the method in accordance with the invention. It can in this respect in particular be a blood treatment apparatus.

In accordance with the invention, the medical apparatus, in particular a blood treatment apparatus for carrying out hemodialysis and/or hemofiltration and/or hemodiafiltration or peritoneal dialysis has a control and processing unit which is programmed and configured for carrying out the method in accordance with the invention for monitoring the at least one impeller pump by means of structure-borne noise analysis. The control and processing unit is for this purpose connected by means of signal lines to the at least one structure-borne noise sensor of the at least one impeller pump. Furthermore, the control and processing unit can be connected by means of signal lines to the drive of the at least one impeller pump for controlling the at least one impeller pump.

If the blood treatment machine is a blood treatment machine for extracorporeal blood treatment, the impeller pump can be used e.g. for pumping blood in the extracorporeal blood circuit and/or for pumping dialysate in the dialysate circuit.

If the blood treatment machine is a peritoneal dialysis machine, the impeller pump can be used for pumping dialysate in the dialysate circuit. In this respect, the dialysate is pumped into the abdominal cavity of the patient where the peritoneum of the patient acts as a semipermeable membrane by which the substances to be removed from the blood pass into the dialysate. The consumed dialysate is accordingly again pumped off out of the abdominal cavity after a dwell time.

Independently of the specific use of the impeller pump, the properties of the impeller pump can be utilized with respect to the air capture.

The amplitude of the measured structure-borne noise increases as the air amount in the impeller pump increases. A corresponding characteristic in the amplitude of the measured structure-borne noise in dependence on the air amount in the impeller pump chamber volume can be stored in the control and processing unit of the blood treatment apparatus so that the amount of the air collected in the impeller pump can be calculated from current measured values of the amplitude of the structure-borne noise. Limit values can be fixed. An alarm signal can be triggered on an exceeding of limit values. The characteristic and/or the limit values apply to the underlying impeller pump in conjunction with a certain blood hose kit and/or dialysate hose kit.

The control and processing unit of the blood treatment apparatus advantageously has a data memory in which a computer program is stored. The program code of the computer program is programmed to evaluate the signals of the at least one structure-borne noise sensor. A reference curve of the structure-borne noise of the at least one impeller pump on disturbance-free operation can be stored in the data memory, with a disturbance of the operation of the impeller pump being concluded on a difference of the measured structure-borne noise from the reference curve. A limit value of the structure-borne noise of the at least one impeller pump can be stored in the data memory on whose exceeding a disturbance of the operation of the impeller pump is concluded.

The characteristic of the amplitude of the measured structure-borne noise in dependence on the air amount in the impeller pump chamber volume can be taken at the start of a blood treatment in disturbance-free operation and limit values can be calculated. It is, however, also possible to use experimentally determined data as the characteristic and/or to fix limit values on the basis of experimental results and to store these fixedly in the memory of the control and processing unit.

The detection in accordance with the invention of air in an impeller pump operated in an extracorporeal blood circuit can be used as a protective measure against the passing of air into the led-off blood flow.

The detection in accordance with the invention of air in the impeller pump can in particular be used for monitoring an impeller pump when it is being directly used as a bubble trap. Temporarily collected air can then be led off from the impeller pump chamber in good time via a venting opening to preempt an impending leading off with the blood flow. Such a venting can in particular be initiated automatically by the control and processing unit when the air amount and/or the measured structure-borne noise of the impeller pump differs from the reference curve and/or exceeds the limit value. A valve actuator can in particular be actuated for this purpose.

The detected air amount furthermore has an influence on the pump rate of the impeller pump. The air quantity detected in accordance with the invention can therefore be taken into account in the balancing of the pumped liquid amount. A corresponding function is advantageously implemented in the control and processing unit.

The medical apparatus in accordance with the invention, in particular the blood treatment apparatus in accordance with the invention, has a control and processing unit and a machine-side drive for an impeller pump.

The present invention furthermore comprises an impeller pump for a medical application, comprising an impeller pump chamber, wherein the impeller pump chamber has a venting opening. The venting opening is preferably provided in a central region of the impeller pump chamber.

The impeller can in this respect have a central region from where vanes extend outwardly via which the fluid is pumped. The venting opening is preferably arranged in a region of the impeller pump chamber which is arranged next to the central region of the impeller in the axial direction.

In this respect, the impeller pump can have a valve by means of which the venting of the impeller pump chamber can be controlled via the venting opening.

In a possible embodiment, the valve is arranged in a coupling area of a cassette in which the impeller pump is integrated.

The present invention furthermore comprises an impeller pump for a medical application comprising an impeller pump chamber, wherein the impeller pump has a structure-borne noise sensor or a coupling point for the structure-borne noise sensor.

The impeller of the impeller pump is preferably magnetically supported so that the impeller only comes into contact involving friction with the conveyed fluid, in particular blood or dialysate, in disturbance-free operation. Such an operation is also called "contactless". A magnet is preferably arranged centrally in the impeller and/or is overmolded by means of plastic in an injection molding process.

The impeller pump in particular serves for carrying out the method in accordance with the invention or for use with a medical apparatus in accordance with the invention, as was shown above.

The impeller pump comprises a housing with an impeller and is preferably a component of the extracorporeal blood hose kit or of a dialysate hose kit, which is in particular designed as a disposable cassette, in particular as a disposable blood cassette or as a disposable dialysate cassette, with the extracorporeal blood hose kit or dialysate hose kit being configured for coupling to a medical apparatus in accordance with the invention, in particular to a blood treatment apparatus.

The present invention furthermore comprises a disposable cassette having an impeller pump in accordance with the present invention, as was described above. The disposable cassette preferably has a coupling area for coupling to a coupling area of a medical apparatus in accordance with the invention, in particular a blood treatment apparatus. In this respect, the impeller pump integrated in the disposable cassette can in particular be coupled to a machine-side drive for the impeller pump. The drive is in this respect preferably arranged in the region of the coupling area of the medical apparatus. Furthermore at least one valve actuator can be provided in the region of the coupling area; a valve of the disposable cassette can be coupled to it and the valve can be actuated by it. The valve can in this respect in particular be able to be used for venting the impeller pump chamber.

The control and processing unit advantageously has a data memory in which a computer program is stored. The program code of the computer program is programmed to control the impeller blood pump and to evaluate and store corresponding structure-borne noise signals.

In this respect, the previously described idea of the invention cannot only be implemented in impeller pumps in a blood circuit or dialysate circuit, but also in any uses of impeller pumps in medical apparatus. The use, however, particularly preferably takes place with impeller pumps in a blood circuit or dialysate circuit.

BRIEF DESCRIPTION OF THE DRAWINGS

Further features, details and advantages of the invention will be explained in more detail with reference to embodiment shown in the drawings. There are shown.

Figure 1:
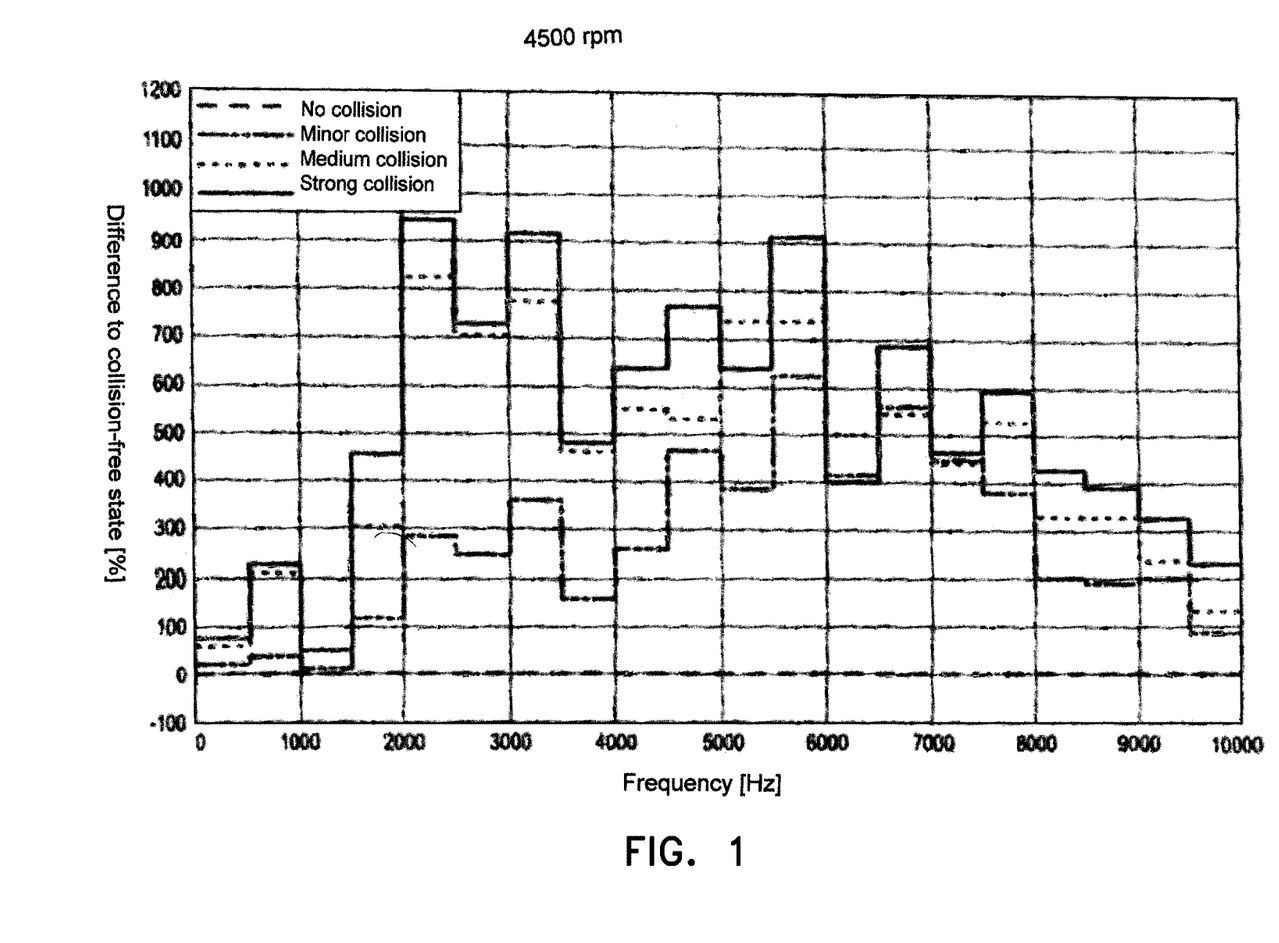
FIG. 1: the measured increase in the structure-borne noise amplitude in dependence on the speed of the impeller pump.

FIG. 1 shows as the result of an experiment with an impeller pump the measured increase in the structure-borne noise amplitude in dependence on the speed of the impeller pump in selected speed ranges normed to the structure-borne noise amplitude in collision-free operation at a speed of 4500 r.p.m. (bottommost straight curve) for the operation of an impeller pump with differently strong collisions of the impeller with the housing. The lower curve shows light collisions; the middle curve medium collisions; and the upper curve strong collisions. It can be seen from this that a significant increase in the structure-borne noise amplitude can already be measured on a slight collision of the impeller, whereby a disturbance can be concluded. It is thus possible to store such experimentally determined data as limit values in the memory of a control and processing unit of the blood treatment apparatus and to compare current measured data of the amplitude of the measured structure-borne noise with the measured values and, on an exceeding of the limit values, to conclude a disturbance of the operation of the impeller pump due to a collision of the impeller.

Figure 2:
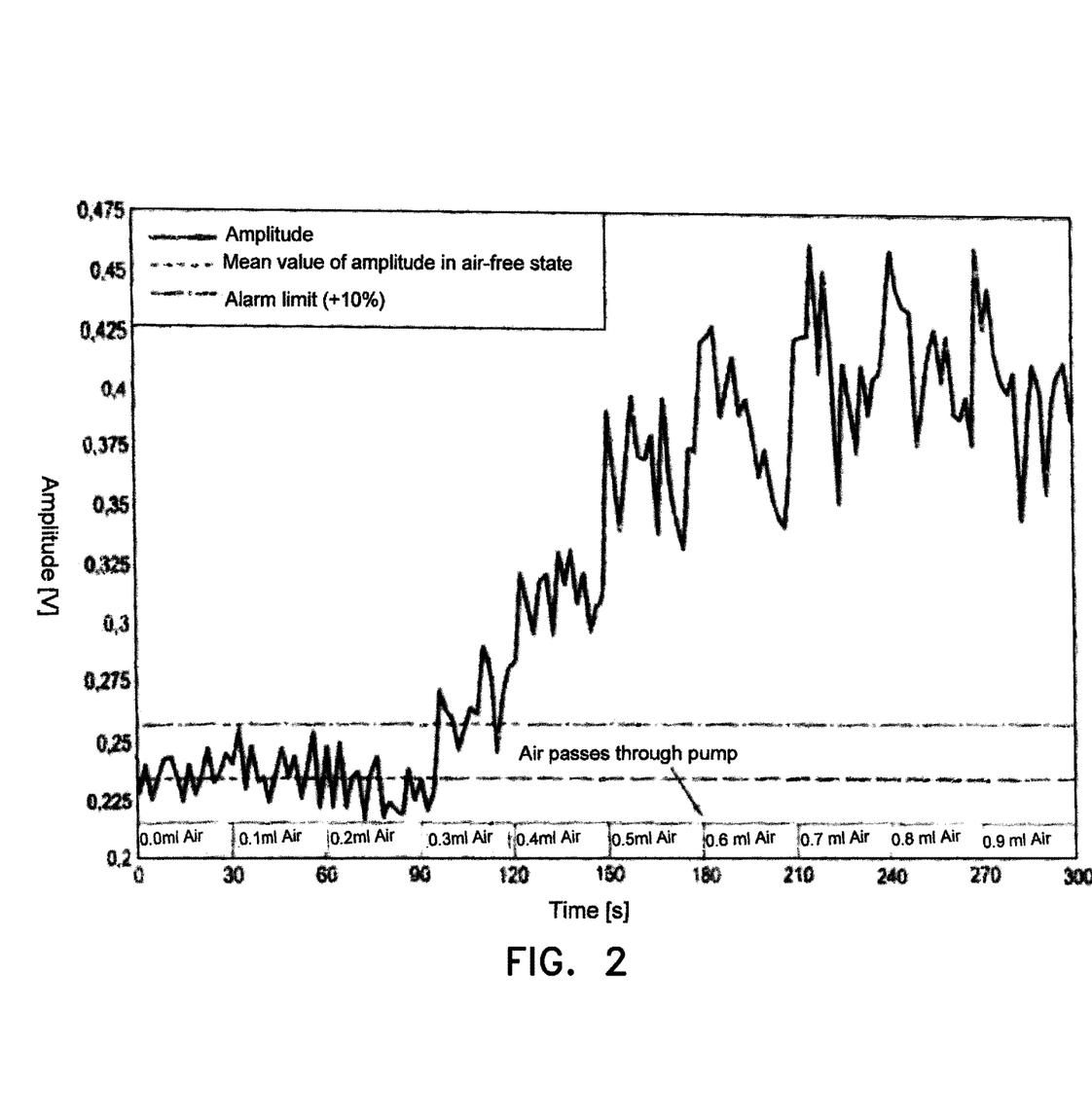
FIG. 2: the measured structure-borne noise in operation of an impeller pump.

FIG. 2 shows measured results of the measured amplitude of the structure-borne noise in the operation of an impeller pump in an experimental structure in dependence on the time, with the air collected in the impeller pump increasing over time. The test rig has the possibility of injecting defined air volumes into the impeller pump and to optically detect the discharge of air bubbles with the blood flow or dialysate flow downstream of the impeller pump. The impeller pump has an impeller pump chamber volume of 3 ml. The speed of the impeller pump amounts to 8000 r.p.m. The evaluated frequency band of the measured structure borne noise amounts to 15 Hz to 150 Hz. FIG. 2 shows the time extent of an experiment with this pump in which a respective additional air amount of 0.1 ml is injected into the impeller pump at intervals of 30 s each. The first interval (from 0 s to 30 s) shows the structure-borne noise amplitude before the first injection of air. An air amount of 0.3 ml has collected in the time interval from 90 s to 120 s, whereby the amplitude of the measured structure-borne noise increases abruptly. At the time t=180 s, the collected air is even carried out with the blood flow or dialysate flow on exceeding the intake capacity, which is optically detected downstream of the impeller pump.

A corresponding characteristic in the amplitude of the measured structure-borne noise in dependence on the air amount in the impeller pump chamber volume can be stored in the control and processing unit of a blood treatment apparatus so that the amount of the air collected in the impeller pump can be calculated from current measured values of the amplitude of the structure-borne noise. Limit values can be fixed. An alarm signal can be triggered on an exceeding of limit values. The characteristic and/or the limit values apply to the underlying impeller pump.

Figure 3:
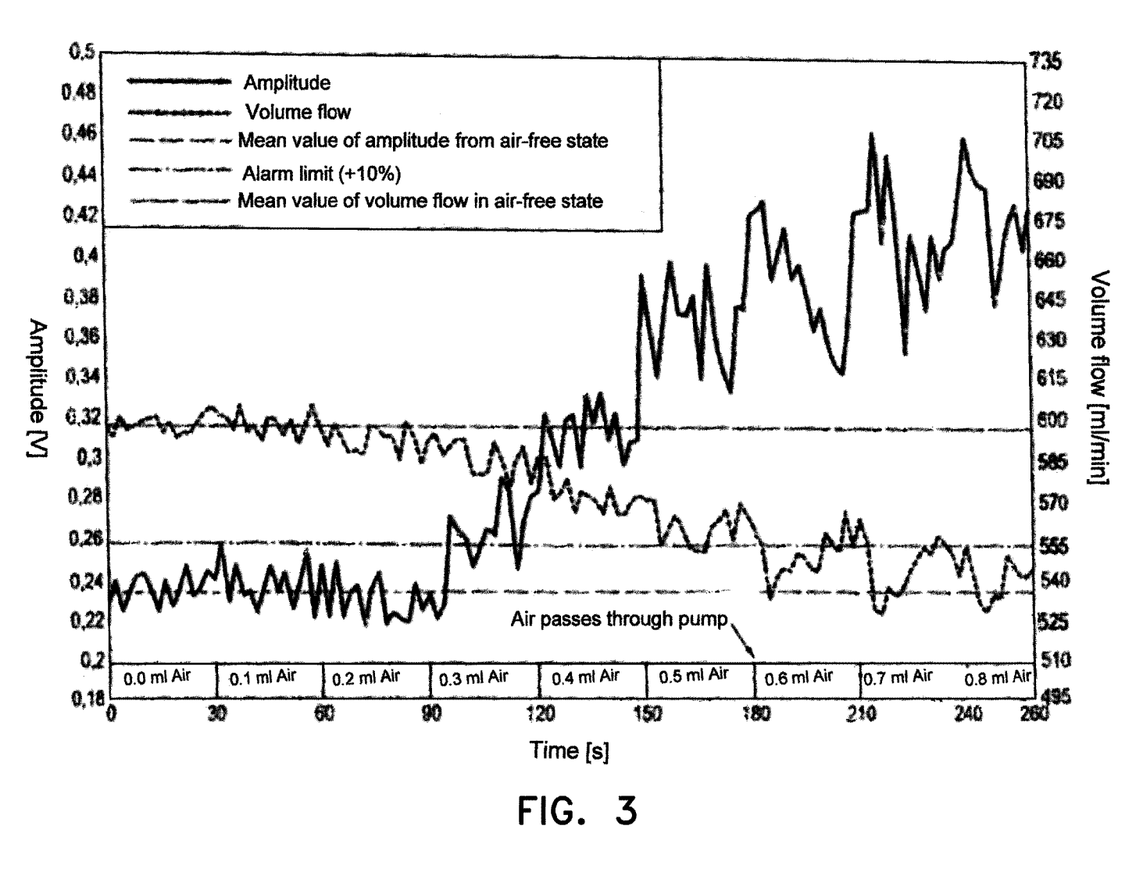
FIG. 3: the measured structure-borne noise amplitude and the measured conveying volume flow on operation of an impeller pump.

FIG. 3 shows a measured structure-borne noise amplitude and a measured conveying volume flow on operation of an impeller pump with an impeller pump chamber volume of 3 ml at a speed of 8000 r.p.m. in dependence on time on a repeated injection of a respective 0.1 ml of air into the impeller pump chamber per time interval of a respective 30 seconds. A measured curve of the volume flow is shown in dependence on time here. This curve extent shows that, in accordance with the invention, a monitoring of the blood flow or dialysate flow through the impeller pump is possible because the blood flow or dialysate flow reduces as the air volume in the impeller pump chamber increases.

Figure 4:
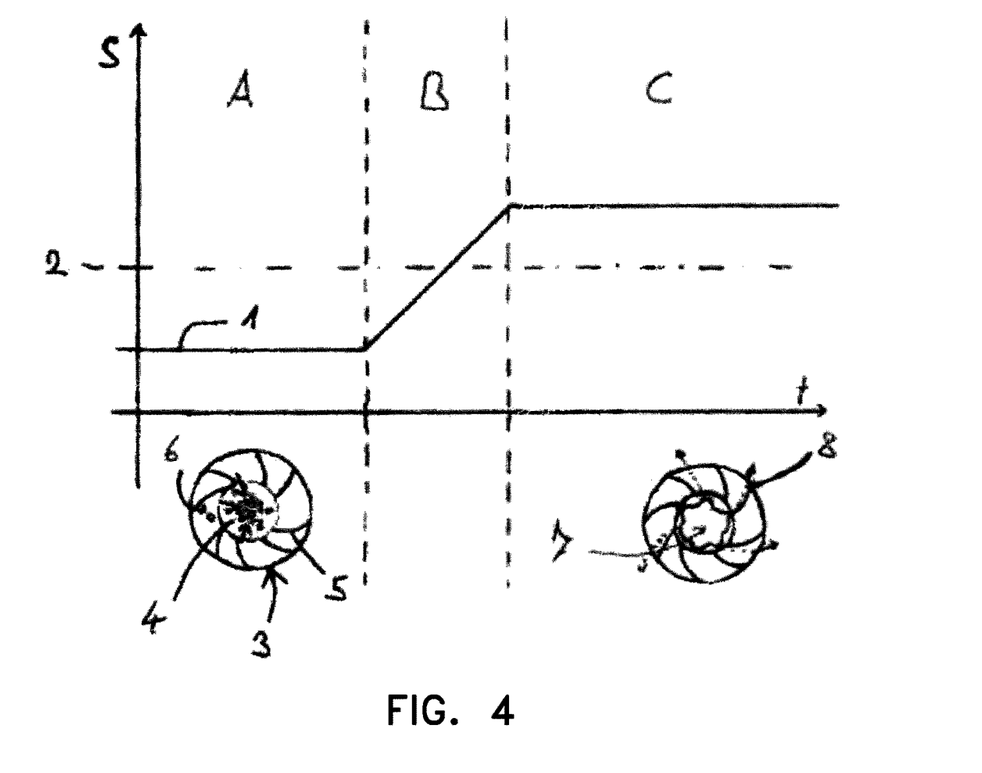
FIG. 4: the structure-borne noise amplitude and the distribution of the air bubbles in the operation of an impeller pump with increased air input.

In FIG. 4, the process of air collection and recognition in the impeller pump chamber is shown again in more detail. In the upper region of FIG. 4, this is shown in this respect in accordance with the structure-borne noise signals S over the time t. The structure-borne noise signal S can in particular be the amplitude of the signal. Evaluation is preferably carried out for a specific frequency band of the structure-borne noise, for example for a frequency band between 15 Hz and 150 Hz.

In the first operating section A, the signal 1 is below the limit value 2, i.e. there is no disturbance. In the region B, an increase in the air amount in the impeller pump chamber can be seen, which results in an increase of the signal 1 and an exceeding of the limit value 2. In the region C, the air amount in the impeller pump chamber exceeds the intake capacity of the impeller pump chamber so that a case of disturbance is present which can be recognized by the high signal level.

In the lower region of FIG. 4, the distributions of the air bubbles within the impeller pump chamber are shown schematically respectively for the phases A and C. In this respect, the respective impeller 3 is reproduced with the respective air bubble distribution, wherein the impeller 3 is configured as an impeller vane having a central region 4 from where vanes 5 extend outwardly.

The process of air collection and recognition in this respect takes place as follows:

In phase A, medium-sized air bubbles 6, which enter into the impeller pump chamber via the fluid flow, are drawn to the central region 4 of the impeller vane 3. The zone of the smallest pressure is in the central region 4. In this respect, centrifugal forces act outwardly and thus hurl particles of large density outwardly, whereas particles having a smaller density migrate inwardly. Since the air bubbles have a smaller density than the pumped fluid, they migrate into the central region 4. In this respect, as long as the collected air bubbles 6 do not exceed a certain limit value, only a low measured signal 1 is defected.

Since the medium-sized air bubbles 6 no longer leave the impeller vane due to the principle involved, they accumulate in the middle in phase B. The presence of other air bubbles results in an agglomeration of the bubbles by which bigger and bigger air bubbles are formed. The measured signal hereby increases so that the increasing air amount in the impeller pump chamber can be detected. In the extreme case, one large bubble 7 is formed in this respect from the individual bubbles, such as is shown on the right in the illustration.

From a specific size of the accumulated bubbles or number of medium-sized bubbles, the impeller pump chamber or the impeller vane cannot take up any further bubbles. This is shown in phase C. In this state, the pump admittedly continues to convey fluid and will optionally also continue to suck in medium-sized air bubbles. They are, however, urged out of the rotor against the centrifugal force and are in this process chopped into very small microbubbles 8. The collection characteristic of the rotor in this respect depends on the speed or on the rotor diameter of the impeller vane (that is on the centrifugal force) and on the bubble diameter. In this respect, only considerably comminuted bubbles can leave the impeller pump at a constant speed. There is a high signal level in this phase.

The three phases A to C can thus be distinguished very easily by means of noise analysis.

In this respect, a venting of the impeller pump chamber is preferably carried out as soon as the signal exceeds the limit value 2. If a state as in phase C is detected, an alarm can furthermore be triggered and/or the machine can be switched into a secure state.

In the previously described embodiment, the invention has been explained with reference to an impeller pump arranged in the blood circuit or dialysate circuit of a blood treatment machine. In the same way, the invention, however, also comprises impeller pumps in other medical applications.

The invention claimed is:

1. A method of monitoring an impeller pump used in a medical application by structure-borne noise analysis comprising the following steps:
    measuring the structure-borne noise arising in the impeller pump;
    comparing the measured structure-borne noise of the impeller pump with a first reference curve and/or with a first limit value;
    concluding a disturbance of the operation of the impeller pump when the measured structure-borne noise of the impeller pump differs from the reference curve and/or exceeds the limit value;
    outputting a signal as a characteristic for a disturbance of the operation of the impeller pump;
    detecting the air quantity in the impeller pump; and
    venting the impeller pump when the detected air quantity and/or the measured structure-borne noise of the impeller pump differs from the reference curve and/or exceeds the limit value.

2. A method in accordance with claim 1 wherein, for which purpose of venting the impeller pump, collected air is led off via a venting opening of the impeller pump chamber.

3. The method in accordance with claim 1, characterized in that collisions of the impeller with the housing of the impeller pump are detected in the impeller pump.

4. The method in accordance with claim 1, wherein the measurement of the structure-borne noise takes place during the operation of the impeller pump.

5. The method in accordance with claim 1, wherein the impeller pump is arranged in a medical apparatus.

6. A medical apparatus, in particular a blood treatment apparatus, comprising a control and processing unit which is programmed and configured for carrying out the method of monitoring the at least one impeller pump by structure-borne noise analysis in accordance with claim 1.

7. The medical apparatus in accordance with claim 6, characterized in that the control and processing unit has a data memory in which a computer program having a program code is stored, with the program code being programmed so that the measured structure-borne noise signals can be evaluated and/or stored.

8. The medical apparatus in accordance with claim 6, characterized in that the blood treatment apparatus has at least one drive unit for driving the at least one impeller pump.

9. The medical apparatus in accordance with claim 6, comprising a structure-borne noise sensor, wherein the structure-borne noise sensor is connected to the control and processing unit by a signal line.

10. The medical apparatus in accordance with claim 9, further comprising a coupling point for the structure-borne noise sensor.

11. The medical apparatus in accordance with claim 6, characterized in that it is a dialysis machine which is configured for carrying out hemodialysis and/or hemofiltration and/or hemodiafiltration and/or peritoneal analysis.

12. A computer program product comprising a program code for a control and processing unit of the blood treatment apparatus wherein the control and processing unit is programmed and configured for carrying out the method of monitoring at least one impeller pump by the structure-borne noise analysis of claim 1.

13. The method in accordance with claim 1, wherein the impeller pump is arranged in an extracorporeal blood circuit of a dialysis machine or in a dialysate circuit of a dialysis machine.

14. A method for monitoring a first impeller pump arranged in an extracorporeal blood circuit for carrying out hemodialysis or hemofiltration or hemodiafiltration and/or a second impeller pump arranged in a dialysate circuit for carrying out hemodialysis or hemofiltration or hemodiafiltration or peritoneal dialysis by a structure-borne noise analysis comprising the following steps:
operating the extracorporeal blood circuit by controlling the first impeller pump and/or operating the dialysate circuit by controlling the second impeller pump;
measuring the structure-borne noise arising in the first impeller pump and/or measuring the structure-borne noise arising in the second impeller pump;
comparing the measured structure-borne noise of the first impeller pump with a first reference curve and/or with a first limit value; and/or
comparing the measured structure-borne noise of the second impeller pump with a second reference curve and/or with a second limit value;
concluding a disturbance of the operation of the first impeller pump when the measured structure-borne noise of the first impeller pump differs from the first reference curve and/or exceeds the first limit value; and/or
concluding a disturbance of the operation of the second impeller pump when the measured structure-borne noise of the second impeller pump differs from the second reference curve and/or exceeds the second limit value;
outputting a signal as a sign for a disturbance of the operation of the first impeller pump and/or outputting a signal as a sign for a disturbance of the operation of the second impeller pump.

15. A medical apparatus, in particular a blood treatment apparatus, comprising a control and processing unit which is programmed and configured for carrying out the method of monitoring the at least one impeller pump by structure-borne noise analysis in accordance with claim 14.

16. An impeller pump for a medical application, in particular for a medical apparatus comprising a control and processing unit which is programmed and configured for carrying out a method of monitoring at least one impeller pump by structure-borne noise analysis comprising the following steps:
measuring the structure-borne noise arising in the impeller pump;
comparing the measured structure-borne noise of the impeller pump with a first reference curve and/or with a first limit value;
concluding a disturbance of the operation of the impeller pump when the measured structure-borne noise of the impeller pump differs from the reference curve and/or exceeds the limit value;
outputting a signal as a characteristic for a disturbance of the operation of the impeller pump;
the impeller pump comprising an impeller pump chamber, characterized in that the impeller pump chamber has a venting opening and at least one of a structure-borne noise sensor and a coupling point for a structure-borne noise sensor.

17. The impeller pump in accordance with claim 16, comprising a valve by which the venting of the impeller pump chamber can be controlled via the venting opening.

18. The impeller pump in accordance with claim 17, wherein the valve is arranged in a coupling area of a cassette into which the impeller pump is integrated.

19. A disposable cassette comprising the impeller pump in accordance with claim 16.

* * * * *